United States Patent [19]

Misaki et al.

[11] Patent Number: 4,524,032

[45] Date of Patent: Jun. 18, 1985

[54] DIRECT FLUORINATION OF ETHERIFIED OR UNETHERIFIED HYDROXY GROUP BEARING AROMATIC COMPOUNDS

[75] Inventors: Susumu Misaki; Sadamu Ishii; Masahiro Suefuji, all of Osaka, Japan

[73] Assignee: Daikin Kogyo Co., Ltd., Osaka, Japan

[21] Appl. No.: 458,095

[22] Filed: Jan. 14, 1983

Related U.S. Application Data

[63] Continuation of Ser. No. 144,020, Apr. 28, 1980, abandoned.

[30] Foreign Application Priority Data

Apr. 28, 1979 [JP] Japan .................... 54-53136

[51] Int. Cl.$^3$ .............. C07C 121/50; C07C 41/00; C07C 39/12
[52] U.S. Cl. ............................ 260/465 F; 568/377; 568/442; 568/643; 568/649; 568/656; 568/717; 568/730; 568/775; 260/694
[58] Field of Search .......... 568/433, 630, 631, 656, 568/775, 377, 694, 442, 643, 649, 717, 730; 260/465 F, 694

[56] References Cited

PUBLICATIONS

Cacace et al., Journ. Amer. Chem. Soc. 100, 3639–3641, (1978).
Barton, Chem. Comm. 1968, p. 806.
Graskaukas, Journ. Org. Chem. 35, No. 3, p. 723, (1970).
Anand, Journ. Org. Chem. 40, 1975, p. 807.

*Primary Examiner*—Ethel G. Love
*Attorney, Agent, or Firm*—Birch, Stewart, Kolasch & Birch

[57] ABSTRACT

A process for direct fluorination of etherified or unetherified hydroxy group-bearing aromatic compounds, which comprises reacting an etherified or unetherified hydroxy group-bearing aromatic compound with fluorine gas to give the corresponding etherified or unetherified hydroxy group and at least one fluorine atom-bearing aromatic compound.

9 Claims, No Drawings

DIRECT FLUORINATION OF ETHERIFIED OR UNETHERIFIED HYDROXY GROUP BEARING AROMATIC COMPOUNDS

This application is a continuation of copending application Ser. No. 144,020, filed on Apr. 28, 1980, now abandoned.

The present invention relates to direct fluorination of etherified or unetherified hydroxy group-bearing aromatic compounds. More particularly, it relates to a process for preparing etherified or unetherified hydroxy group and fluorine atom-bearing aromatic compounds by direct fluorination of the corresponding etherified or unetherified hydroxy group-bearing aromatic compounds with fluorine gas.

Etherified or unetherified hydroxy group and fluorine atom-bearing aromatic compounds are useful as intermediates in the synthesis of medicines, agricultural chemicals, dyestuffs, etc. For instance, fluorinated salicylaldehyde is useful as an intermediate in the production of cobalt chelate compounds which can be per se used as oxygen-releasing agents.

There are some processes known for the fluorination of aromatic compounds, one of which is the so-called Schiemann process which comprises nitrating an aromatic compound, reducing the resulting nitro compound, diazotiating the resultant amino compound with sodium nitrite in tetrafluoroboric acid or hydrofluoric acid thermally decomposing the thus obtained diazonium salt. Another process is the so-called halogen exchange process which comprises fluorinating a chlorinated aromatic compound having an electron-attracting group, such as a nitro group, with an alkali metal fluoride in an aprotic polar solvent such as dimethylformamide. These conventional processes are, however, hardly applicable to industrial production, because they require a large quantity of expensive starting materials and many reaction steps and afford only low yield of the desired products. Particularly, the Schiemann process is disadvantageous because it requires the handling of a highly unstable diazonium salt.

In addition to the above conventional processes, there are known electrolytic fluorination, fluorination with polyfluorinated metals, etc. The major products in these fluorination processes are, however, polyfluorinated compounds.

Recently, a direct fluorination process in a liquid phase with fluorine gas has been developed for fluorination of aromatic compounds (J. Org. Chem., 35, 723 (1970)). Further, fluorination of aromatic compounds using some special fluorinating agents such as xenone difluoride has been reported (J. Org. Chem., 40, 807 (1975); Chem. Commun., 1968, 806). However, these processes are also hardly applicable to industrial production except that certain specific compounds as in U.S. Pat. No. 4,082,752 are used as the starting materials, because the reaction conditions of these processes are difficult to control, they require the use of dangerous reagents and afford only low yields of the desired products.

As a result of an extensive study, it has now been found that etherified or unetherified hydroxy group-bearing aromatic compounds can be directly fluorinated by treatment with fluorine gas to give the corresponding etherified or unetherified hydroxy group and fluorine atom-bearing aromatic compounds in sufficiently good yields. It is notable that such direct fluorination can usually afford a monofluorinated compound, particularly the one fluorinated ortho or para to the etherified or unetherified hydroxy group on the aromatic ring, as the major product.

According to the present invention, there is provided a process for the direct fluorination of etherified or unetherified hydroxy group-bearing aromatic compounds, which comprises reacting an etherified or unetherified hydroxy group-bearing aromatic compound with fluorine gas to give the corresponding etherified or unetherified hydroxy group and a fluorine atom-bearing aromatic compound.

The starting etherified or unetherified hydroxy group-bearing aromatic compound comprises an aromatic ring and at least one etherified or unetherified hydroxy group thereon. The aromatic ring may be carbocyclic or heterocyclic, and it is usually a benzene ring. The etherified or unetherified hydroxy group may be hydroxy or lower alkoxy (e.g. methoxy, ethoxy, propoxy). Thus, the preferred examples of the etherified or unetherified hydroxy group-bearing aromatic compound are representable by the formula:

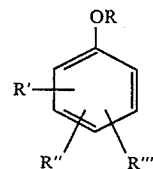

wherein R is hydrogen or lower alkyl and R', R" and R''' are each hydrogen, halogen, lower alkyl, lower alkoxy, hydroxy, nitro, cyano, formyl, phenyl, hydroxyphenyl or lower alkoxyphenyl. Those compounds wherein no substituent is present at the o- and/or p-positions to —OR are particularly favorable.

The fluorination may be carried out by treatment of the etherified or unetherified hydroxy group-bearing aromatic compound with fluorine gas, preferably in a solvent inert under the reaction conditions. When the etherified or unetherified hydroxy group-bearing aromatic compound is per se in a liquid state, the use of the inert solvent is not necessarily required.

Examples of the inert solvent are water, halogenated hydrocarbons (e.g. chlorinated hydrocarbons, chlorofluorinated hydrocarbons, perfluorinated hydrocarbons), acetonitrile, glymes (e.g. diglyme, triglyme, tetraglyme), lower alkanoic acids (e.g. acetic acid, propionic acid), lower haloalkanoic acids (e.g. trifluoroacetic acid), lower alkanols (e.g., methanol, ethanol), lower haloalkanols (e.g. trifluoroethanol), ethers (e.g. dimethyl ether, diethyl ether, perfluoroethers), ketones (e.g. hexafluoroacetone hydrate), perfluorodecalin, perfluorotributylamine, hydrogen fluoride, hydrofluoric acid, sulfuric acid, phosphoric acid, etc.

Fluorine gas may be introduced as such into the reaction system. Preferably, however, it is diluted with an inert gas (e.g. nitrogen, argon) and then introduced into the reaction system.

The fluorination is usually effected at a temperature between the solidifying point of the inert solvent and the boiling point of the inert solvent. Since the reaction proceeds with generation of heat, agitation of the reaction mixture is preferred to eliminate the generated heat and to smoothly accomplish the fluorination. A dehydrofluorinating agent may be incorporated into the reaction system so that side-reactions can be noticeably suppressed. Examples of the dehydrofluorinating agent are molecular sieve, sodium fluoride, etc.

The fluorination can be effected batchwise or continuously; for instance, the continuous method by countercurrently contacting the starting material dissolved in the inert solvent with fluorine gas may be adopted.

The conversion of the starting material may be retained at a certain level (e.g. 50 to 60%). After recovery of the fluorinated product from the reaction mixture, the residue containing the unreacted starting material is again subjected to fluorination. By such method, the by-production of unfavorable polymeric materials can be remarkably decreased.

As a result of the fluorination according to the process of this invention, there is produced a fluorinated product, i.e. the etherified or unetherified hydroxy group and fluorine atom-bearing aromatic compound corresponding to the starting material. Usually, the fluorination takes place at the o- or p-position to the etherified or unetherified hydroxy group.

The proportion of the o-fluorinated product and the p-fluorinated product can be controlled appropriately depending on various factors, particularly on the reaction temperature. For instance, in case of the starting material being phenol, the fluorination in tetraglyme at a temperature of $-40°$ to $10°$ C. can afford the o-fluorinated product in a higher proportion with a lower reaction temperature. Further, the progress of the reaction gives the p-fluorinated product in a higher proportion. Furthermore, the suitable selection of the inert solvent as the reaction medium affords a considerable influence on the proportion of the o-fluorinated product and the p-fluorinated product. For instance, in case of the starting material being cresols, the use of tetraglyme gives the o-fluorinated product in a higher proportion than the use of acetonitrile.

The fluorinated product obtained in the process of the invention is the etherified or unetherified hydroxy group and at least one fluorine atom-bearing aromatic compound, which comprises an aromatic ring and at least one etherified or unetherified hydroxy group and at least one fluorine atom thereon. The aromatic ring may be carbocyclic or heterocyclic, but preferably it is a benzene ring. The etherified or unetherified hydroxy group is usually hydroxy or lower alkoxy (e.g. methoxy, ethoxy, propoxy). Although the major product is ordinarily a monofluorinated compound, there are obtainable polyfluorinated compounds as the byproducts. Preferred examples of the fluorinated product are represents by the formula:

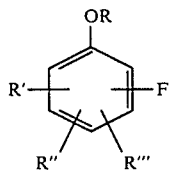

wherein R, R', R" and R'" are each as defined above.

As understood from the above descriptions, the process of this invention is much more advantageous than the conventional processes in giving the desired fluorinated products in better yields with suitable regulation of the proportion of the fluorinated products.

Practical and presently preferred embodiments of the present invention are illustratively shown in the following examples.

EXAMPLE 1

A solution of phenol (6.85 g) in tetraethylene glycol dimethyl ether (tetraglyme) (61.65 g) is charged in a stainless steel made reactor and cooled to a temperature of $-10°$ to $-3°$ C. with vigorous stirring. Then, fluorine gas diluted with nitrogen is introduced into the solution. The reaction is terminated when a 83.3% conversion of phenol is achieved. The reaction mixture is washed with water and an alkaline solution and fractionally distilled to give o-fluorophenol (B.P., 162° C.) in a yield of 57% and p-fluorophenol (B.P., 185.5° C.) in a yield of 14.2% with difluorophenol and high boiling materials in small yields.

EXAMPLE 2

In the same manner as in Example 1 but using acetonitrile in place of tetraglyme, the reaction is carried out and terminated when a 62.3% conversion of phenol is achieved. From the reaction mixture, there are obtained o-fluorophenol in a 39.6% yield and p-fluorophenol in a 17.5% yield with small amounts of difluorophenol and high boiling materials.

EXAMPLE 3

In the same manner as in Example 2 but adopting a temperature of $-40°$ C. in place of a temperature of $-10°$ to $-3°$ C., the reaction is carried out and terminated when a 64.2% conversion of phenol is achieved. From the reaction mixture, there are obtained o-fluorophenol in a 52.5% yield and p-fluorophenol in a 13.4% yield with small amounts of difluorophenol and high boiling materials.

EXAMPLE 4

In the same manner as in Example 1 but using anisole in place of phenol, the reaction is carried out to give monofluoroanisole in a 60% yield with small amounts of difluoroanisole and high boiling materials.

EXAMPLES 5 TO 11

The reaction is carried out in the same manner as in Example 1 but adopting the temperature and/or using the starting material and the solvent as shown in Table 1 and terminated when a conversion shown in Table 1 is achieved. While in Example 8 fluorine gas was used without being diluted with nitrogen, fluorine gas was previously diluted with nitrogen in other Examples. From the reaction mixture, there are obtained the fluorinated compounds as shown in Table 1.

TABLE 1

| Example | Starting material | Reaction temperature (°C.) | Solvent | Conversion (%) | Fluorinated compound | Yield (%) | B.P. (°C.) |
|---|---|---|---|---|---|---|---|
| 5 | o-Cresol | −10 | Acetonitrile | 84.6 | 2-Methyl-6-fluorophenol | 17.3 | 162–164 |
|   |   |   |   |   | 2-Methyl-4-fluorophenol | 13.3 | 86/14 mmHg |
| 6 | p-Cresol | −20 | Acetonitrile | 78.4 | 4-Fluoro-4-methyl-2,5-cyclohexadien-1-one | 10.0 | 45/17 mmHg 58–59 |
|   |   |   |   |   | 2-Fluoro-4-methylphenol | 26.8 | 6m-Hg |

TABLE 1-continued

| Example | Starting material | Reaction temperature (°C.) | Solvent | Conversion (%) | Fluorinated compound | Yield (%) | B.P. (°C.) |
|---|---|---|---|---|---|---|---|
| 7 | p-Cresol | −20 | Tetraglyme | 70.3 | 4-Fluoro-4-methyl-2,5-cyclohexadien-1-one | 17.0 | 58–59/6 mmHg |
|  |  |  |  |  | 2-Fluoro-4-methylphenol | 19.4 | 45/17 mmHg |
| 8 | p-Cresol | −10 | Acetonitrile | 77.8 | 4-Fluoro-4-methyl-2,5-cyclohexadien-1-one | 13.3 | 58–59/6 mmHg |
|  |  |  |  |  | 2-Fluoro-4-methylphenol | 21.0 | 45/17 mmHg |
| 9 | m-Cresol | −20 | Tetraglyme | 47.0 | 3-Methyl-6-fluorophenol | 17.5 | 110–112 |
|  |  |  |  |  | 3-Methyl-4-fluorophenol | 1.9 | 76/5 mmHg |
| 10 | 2,3-Xylenol | −5 | Acetonitrile | 77.6 | 2,3-Dimethyl-4-fluorophenol and 2,3-dimethyl-6-fluorophenol | 31.1 | — |
|  |  |  |  |  | 2,3-Dimethyl-4,6-difluorophenol | 1.4 | — |
| 11 | 2,6-Xylenol | −5 | Acetonitrile | 66.4 | 2,6-Dimethyl-4-fluorophenol | 27.4 | — |

EXAMPLE 12

Into a 100 ml four-necked flask equipped with a stirrer, a thermometer, a condenser and a gas-inlet tube, salicylaldehyde (5.0 g; 0.041 mole), acetonitrile (45 g) and sodium fluoride (2 g) are charged. Then, fluorine gas (0.062 mole) diluted with nitrogen is introduced into the flask over 4 hours under cooling at 2° to 4° C. The reaction is terminated when a conversion of salicylaldehyde reaches 93.8%. Acetonitrile is distilled off. By gas chromatography, the resulting product (1.70 g) is confirmed to contain 3-fluorosalicylaldehyde (B.P., 85°–88° C./10 mmHg; M.P., 65°–66° C.) (0.97 g; 18.2%), 5-fluorosalicylaldehyde (M.P., 81°–83° C.) (0.42 g; 7.9%), the unreacted starting material (0.31 g) and a small amount of difluorosalicylaldehyde.

EXAMPLE 13

Salicylaldehyde (5.0 g; 0.041 mole) is dissolved in anhydrous hydrofluoric acid (57.5 g), and fluorine gas (0.062 mole) diluted with nitrogen is introduced therein at 2° to 4° C. over 60 minutes. Then, hydrofluoric acid is distilled off. By gas chromatography, the resulting product (6.0 g) is confirmed to contain salicylaldehyde (1.91 g; 33.3%), 5-fluorosalicylaldehyde (0.41 g; 7.1%), a small amount of the unreacted starting material and a small amount of difluorosalicylaldehyde.

EXAMPLE 14

Salicylaldehyde (5.0 g; 0.041 mole) is dissolved in 1,1,2-trichloro-1,2,2-trifluoroethane (45 g), and fluorine gas (0.062 mole) diluted with nitrogen is introduced therein at 0° to 5° C. over 90 minutes. Then, 1,1,2-trichloro-1,2,2-trifluoroethane is distilled off. By gas chromatography, the resulting product (1.96 g) is confirmed to contain 3-fluorosalicylaldehyde (1.36 g; 25.6%), 5-fluorosalicylaldehyde (0.20 g; 3.8%), the unreacted starting material (0.40 g) and a small amount of difluorosalicylaldehyde.

What is claimed is:

1. A process for the direct fluorination of hydroxy group-bearing aromatic compounds which comprises reacting a hydroxy group-bearing aromatic compound with fluorine gas in an inert solvent at a temperature of from −40° to 10° C. to give the corresponding product having at least one hydroxy group and at least one fluorine atom thereon.

2. The process according to claim 1, wherein the inert solvent is acetonitrile, a glyme or a halogenated hydrocarbon or a mixture thereof.

3. The process according to claim 2, wherein the glyme is diglyme, triglyme or tetraglyme.

4. The process according to claim 1, wherein the fluorine gas is diluted with an inert gas prior to reaction with said hydroxy group-bearing aromatic compound.

5. The process according to claim 1, wherein the aromatic compound reactant is a compound comprising an aromatic ring having at least one hydroxy group thereon.

6. The process according to claim 5, wherein said aromatic ring is a benzene ring.

7. The process according to claim 5, wherein the aromatic compound reactant is represented by the formula:

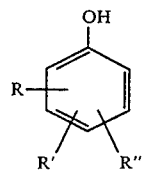

wherein R, R' and R" are each hydrogen, halogen, lower alkoxy, hydroxy, nitro, cyano, formyl, phenyl, hydroxyphenyl or lower alkoxyphenyl.

8. The process according to claim 1, wherein said product is represented by the formula:

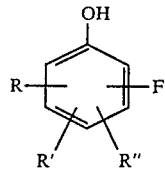

wherein R, R' and R" are each hydrogen, halogen, lower alkyl, lower alkoxy, hydroxy, nitro, cyano, formyl, phenyl, hydroxyphenyl or lower alkoxyphenyl.

9. The process according to claim 1, wherein the aromatic compound reactant has at least one open position with no substituent on at least one of the ortho and para positions to said hydroxy group and said product has a fluorine atom on at least one of said open positions.

* * * * *